(12) United States Patent
Williams

(10) Patent No.: US 6,719,557 B1
(45) Date of Patent: *Apr. 13, 2004

(54) ORTHODONTIC APPLIANCE CONTRACTION CONNECTOR

(76) Inventor: Michael O. Williams, 58 Shoreline La., Gulfport, MS (US) 39053

( * ) Notice: Subject to any disclaimer, the term of this patent is extended or adjusted under 35 U.S.C. 154(b) by 50 days.

This patent is subject to a terminal disclaimer.

(21) Appl. No.: 09/975,633

(22) Filed: Oct. 12, 2001

Related U.S. Application Data

(63) Continuation-in-part of application No. 09/750,527, filed on Dec. 29, 2000, now Pat. No. 6,520,772, which is a continuation-in-part of application No. 09/598,766, filed on Jun. 22, 2000, now Pat. No. 6,402,510, which is a continuation-in-part of application No. 09/406,426, filed on Sep. 27, 1999, now Pat. No. 6,241,517, which is a continuation-in-part of application No. 09/143,071, filed on Aug. 28, 1998, now Pat. No. 6,036,488, which is a continuation-in-part of application No. 09/065,344, filed on Apr. 23, 1998, now Pat. No. 5,919,042.

(51) Int. Cl.$^7$ .................................... A61C 3/00
(52) U.S. Cl. ........................... 433/19; 433/18
(58) Field of Search .................. 433/19, 18, 21, 433/22

(56) References Cited

U.S. PATENT DOCUMENTS

| | | | |
|---|---|---|---|
| 360,695 A | 4/1887 | Holmes | 433/7 |
| 3,798,773 A | 3/1974 | Northcutt | 433/19 |
| 4,144,643 A | 3/1979 | Krygier | 433/7 |
| 4,245,986 A | 1/1981 | Andrews | 433/5 |
| 4,347,054 A | 8/1982 | Kraus et al. | 433/7 |
| 4,373,913 A | 2/1983 | McAndrew | 433/7 |
| 4,382,783 A | 5/1983 | Rosenberg | 433/19 |
| 4,424,032 A | 1/1984 | Howe | 433/19 |
| 4,462,800 A | 7/1984 | Jones | 433/19 |
| 4,472,139 A | 9/1984 | Rosenberg | 433/19 |
| 4,482,318 A | 11/1984 | Forster | 433/7 |
| 4,723,910 A | 2/1988 | Keller | 433/7 |
| 4,795,342 A | 1/1989 | Jones | 433/19 |
| 5,064,370 A | 11/1991 | Jones | 433/21 |
| 5,074,784 A | * 12/1991 | Sterrett et al. | 433/18 |
| 5,352,116 A | 10/1994 | West | 433/19 |
| 5,505,616 A | * 4/1996 | Harwell | 433/21 |
| 5,645,422 A | 7/1997 | Williams | 433/7 |
| 5,678,990 A | * 10/1997 | Rosenberg | 433/19 |
| 5,769,631 A | 6/1998 | Williams | 433/7 |
| 6,012,920 A | * 1/2000 | Woo | 433/19 |
| 6,162,051 A | * 12/2000 | Brehm et al. | 433/19 |

FOREIGN PATENT DOCUMENTS

DE  29619489  9/1996

OTHER PUBLICATIONS

The Herbst Appliance, Chapter 14, pp. 259–279, Feb. 13, 1998.

* cited by examiner

*Primary Examiner*—John J. Wilson
(74) *Attorney, Agent, or Firm*—Paul M. Denk

(57) ABSTRACT

A contracting connector between a maxillary apparatus and mandibular apparatus to treat an underbite. The connector has a telescoping outer sheath connected at its posterior end to the maxillary apparatus. A rod is slidingly engaged in the sheath. And connected at its anterior end to the mandibular apparatus. A spring connected between the rod and the posterior end of the sheath exerts adjustable contraction pressure on the rod and thus the mandible. In another embodiment, the rod has separate anterior and posterior segments The posterior segment of the rod is attached to the maxillary apparatus and the anterior segment is attached to the mandibular apparatus A spring connected between the anterior and posterior segments exerts adjustable contracting pressure on the two rod segments and thus on the maxilla and the mandible. In either embodiment the contracting pressure on the spring is adjusted by changing the length of the telescoping outer sheath. An improved channel lock for connectors also is disclosed.

27 Claims, 13 Drawing Sheets

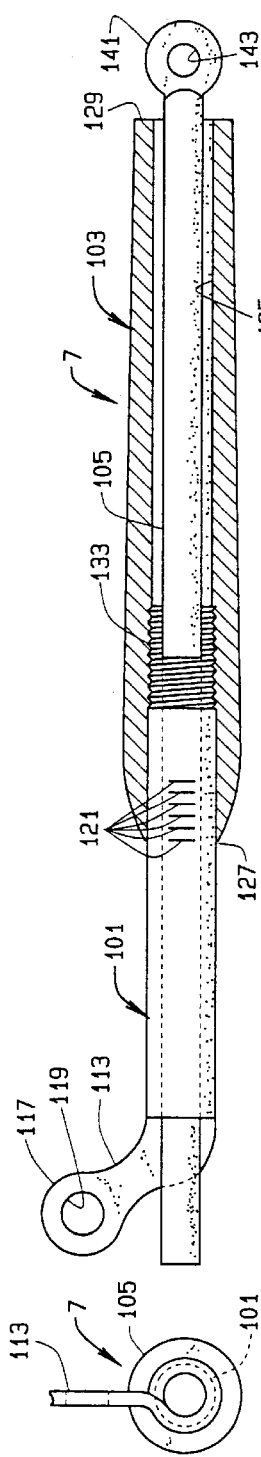

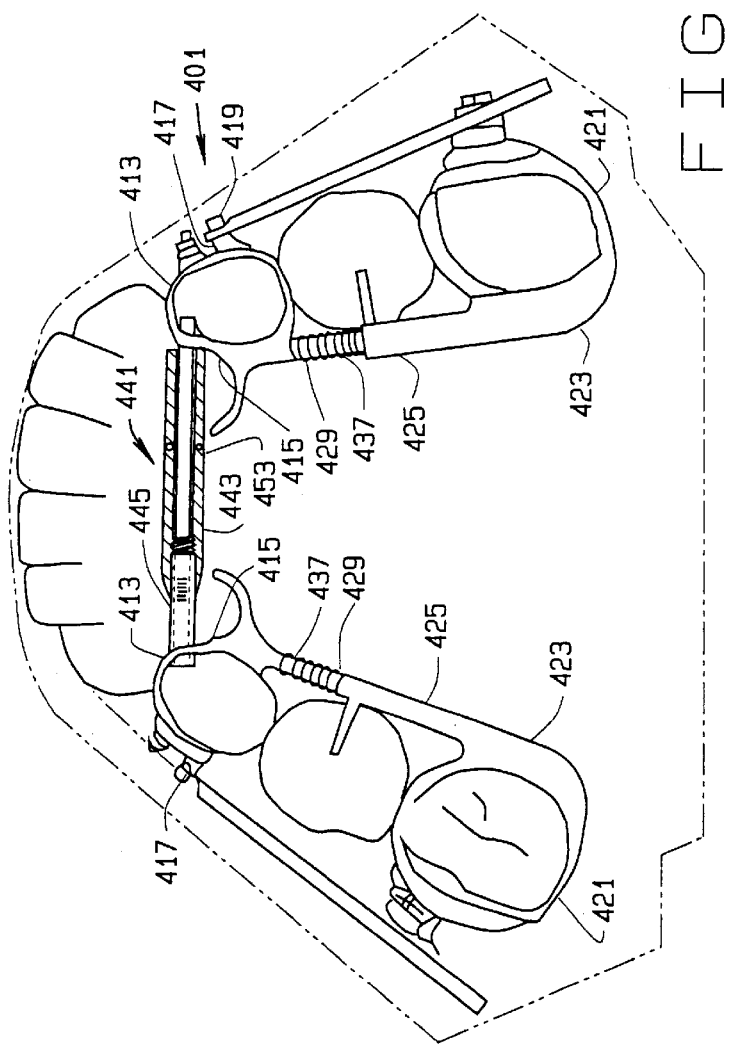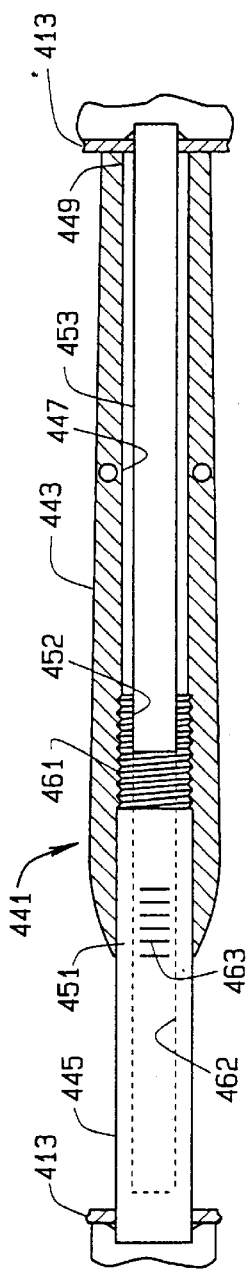

FIG. 19
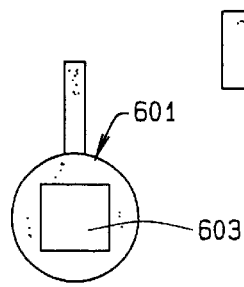
FIG. 20
FIG. 21
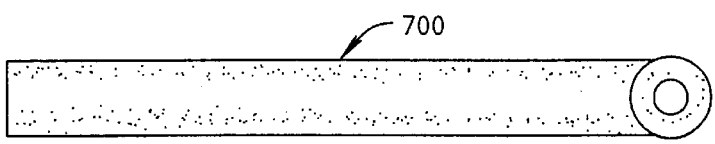
FIG. 22
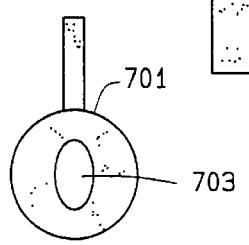
FIG. 23
FIG. 24
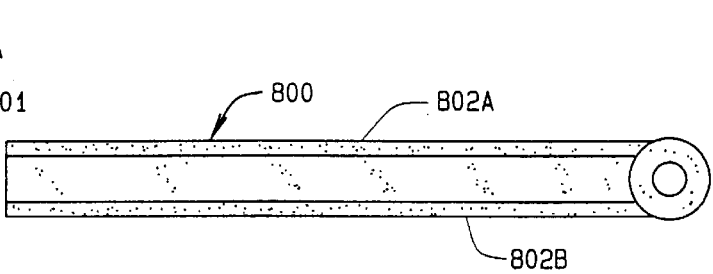
FIG. 25
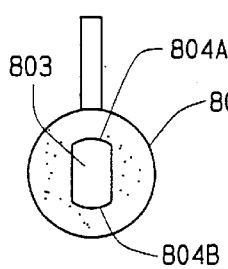
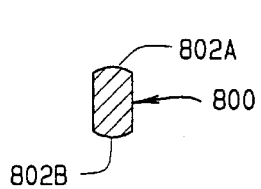
FIG. 26
FIG. 27

ORTHODONTIC APPLIANCE CONTRACTION CONNECTOR

CROSS-REFERENCE TO RELATED APPLICATIONS

This application is a continuation-in-part of application Ser. No. 09/750,527, filed Dec. 29, 2000 (now U.S. Pat. No. 6.520,772) which is a continuation in part of Ser. No. 09/598,766, filed Jun. 22, 2000, entitled Buccal Tipping-Resistant Mandibular And Maxillary Arch Expander (now U.S. Pat. No. 6,402,510) which is a continuation-in-part of application Ser. No. 09/406,426, filed Sep. 27, 1999 (now U.S. Pat. No. 6,241,517), which is a continuation-in-part of application Ser. No. 09/143,071, filed Aug. 28, 1998 and entitled Pivotal Mounting Boss For Mandibular And Maxillary Arch Expander And Jaw Repositioner, now U.S. Pat. No. 6,036,488, which, in turn, is a continuation-in-part of application Ser. No. 09/065,344, filed Apr. 23, 1998 and entitled For Mandibular And Maxillary Arch Expander And Jaw Repositioner, now U.S. Pat. No. 5,919,042, all of which are incorporated herein by reference. The invention is further related to the inventions shown and described in U.S. Pat. No. 5,645,422 entitled Mandibular And Maxillary Arch Expander, and U.S. Pat. No. 5,769,631, entitled Orthodontic Device, both of which are incorporated herein by reference.

STATEMENT REGARDING FEDERALLY SPONSORED RESEARCH OR DEVELOPMENT

Not Applicable.

BACKGROUND OF THE INVENTION

This invention relates generally to orthodontic devices and, in particular, to an improved device for treating an underbite, specifically a Class III malocclusion.

Class III malocclusions occur in about 4% of the Caucasian population but are quite prevalent in the Asian populations. Generally, Class III malocclusion or underbite in an adult or non-growing patient is corrected by an orthognathic surgical operation which requires surgically breaking the jaw and moving the maxilla anteriorly or moving the mandible posteriorly, or both. It would be advantageous, therefore, to have an orthodontic appliance that can be employed to correct underbite in an older or non-growing patient in order to avoid oral surgery.

BRIEF SUMMARY OF THE INVENTION

In this application, a new a contracting sheath connector for attachment between the maxilla and mandible is provided. The contracting sheath can be connected between a maxillary molar or maxillary appliance and a mandibular appliance.

The contracting sheath includes a hollow posterior tube, a hollow anterior tube, and a rod extending through the two tubes. The anterior and posterior tubes are threadably connected so that the overall length of the advancing sheath can be selectively altered. An attachment is provided at a forward end of the posterior tube to pivotally mount the posterior tube to a tooth band. Another attachment is provided at the back end of the rod to pivotally connect the rod to a second tooth band. A spring is provided which extends between a forward end of the anterior tube and a forward end of the posterior tube. The spring urges the anterior tube rearwardly relative to the posterior tube to compensate for jaw pressure and to help prevent the jaw pressure from threading the anterior tube rearwardly.

In one embodiment, the posterior tube is externally threaded and the anterior tube is internally threaded. In this embodiment, the spring is journaled about the posterior tube. The posterior tube is provided with a stop forwardly of the end of the anterior tube, and the spring is positioned between the posterior tube stop and the forward end of the anterior tube. In a second embodiment, the posterior tube is internally threaded, and the anterior tube is externally threaded. In this embodiment, the spring is received within the hollow posterior tube and is journaled about the rod.

The expansion complex includes an outer housing and an advancing member which is telescopically received in the outer housing. The two portions of the expansion complex are received in opposed halves of a plate which fits against the mandibular or maxillary arch.

The outer housing includes side walls, a top, a bottom, a back, and an open front. A channel is formed in the housing top and extends rearwardly from the front of the housing. A threaded rod extends forwardly from the housing back wall beneath the channel to be accessible through the channel. At least one post (and preferably two posts) extend from the housing back wall parallel to the threaded rod.

The advancing member includes side walls, a bottom, a top, and a front wall. The advancing member is sized and shaped to beslidably received in the outer housing. A channel is formed in the advancing member top and extends rearwardly from the front wall. The advancing member channel is aligned with the outer housing channel.

To move the advancing member, an activation nut is threadably received on the threaded rod. The nut is accessible through the channels and movable along the threaded rod by rotation of the nut. An activation wing has a first plate slidably received on the threaded rod in front of the activation nut and a second plate slidably received on the post. The first and second plates are operatively connected to each other, and movement of the activation nut moves the first plate, and hence the second plate, relative to the housing and the advancing member. A spring is journaled about the post between the activation wing second plate and the advancing member front wall. When the spring is compressed, it effectively applies a pressure to the arch to force expansion of the arch.

Guides are provided to facilitate movement of the advancing member relative to the housing. The grooves of the outer housing and the advancing member are both defined by sloped walls, and the sloped walls of the advancing member channel are adjacent the sloped walls of the housing channel. Additionally, a groove is provided in the bottom surface of the advancing member and a corresponding rib is formed on the inner surface of the housing bottom. The rib and groove interaction, as well the interaction of the sloped walls, act as the guides for the movement of the advancing member.

BRIEF DESCRIPTION OF THE SEVERAL VIEWS OF THE DRAWINGS

FIG. 2 is a side elevational view of the telescoping assembly, partially in cross-section;

FIG. 3 is a front plan view of the telescoping assembly;

FIG. 4 is a side elevational view of a rod of the telescoping assembly;

FIG. 5 is a front elevational view of the rod;

FIG. 6 is a side elevational view of a posterior tube of the telescoping assembly;

FIG. 7 is a rear elevational view of the posterior tube;

FIG. 8 is a side elevational view of an anterior tube of the telescoping assembly;

FIG. 9 is a front end elevational view of the anterior tube;

FIG. 10 is a back end elevational view of the anterior tube;

FIG. 15 is a top plan view, partly in cross-section, of an alternative mandibular arch expander using a telescoping assembly;

FIG. 16 is an enlarged cross-sectional view of the telescoping assembly of FIG. 15;

FIG. 19 is a side elevational view of an alternative embodiment of a rod of the telescoping assembly;

FIG. 20 is a front elevational view of the rod;

FIG. 21 is a rear elevational view of an alternative embodiment of the posterior tube;

FIG. 22 is a side elevational view of another alternative embodiment of a rod of the telescoping assembly;

FIG. 23 is a front elevational view of the rod;

FIG. 24 is a rear elevational view of another alternative embodiment of the posterior tube;

FIG. 25 is a side elevational view of yet another alternative embodiment of a rod of the telescoping assembly;

FIG. 26 is a front elevational view of the rod;

FIG. 27 is a rear elevational view of yet another alternative embodiment of the posterior tube;

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes adaptations, and variations of the invention, including what I presently believe is the best mode of carrying out the invention.

Figure 1:
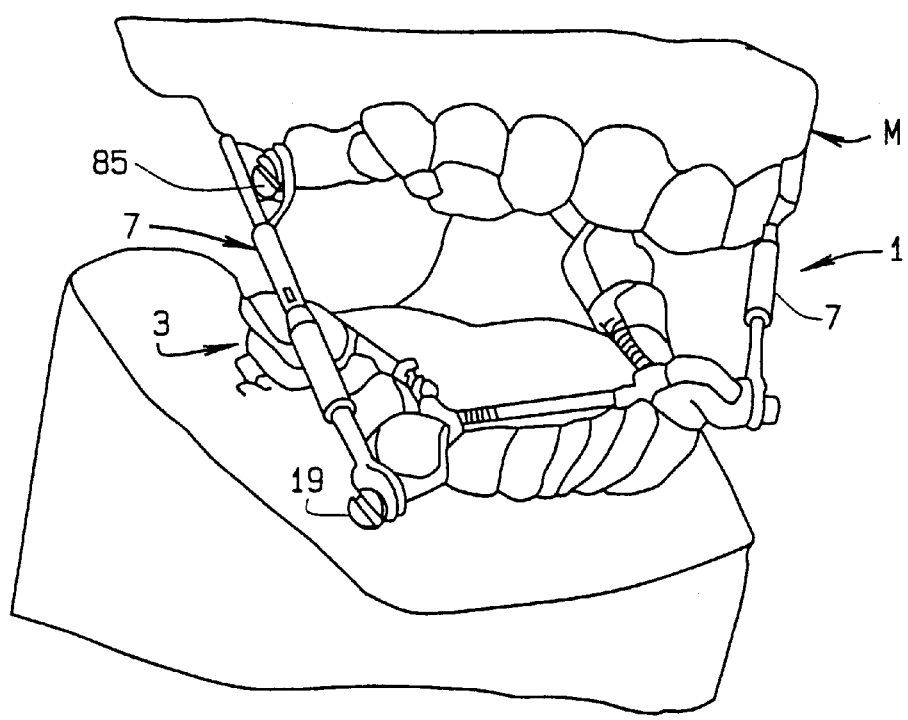
FIG. 1 is a perspective view of a mandibular arch expander and maxillary arch expander which are shown mounted in a mold and connected by a telescoping assembly.
Figure 1A:
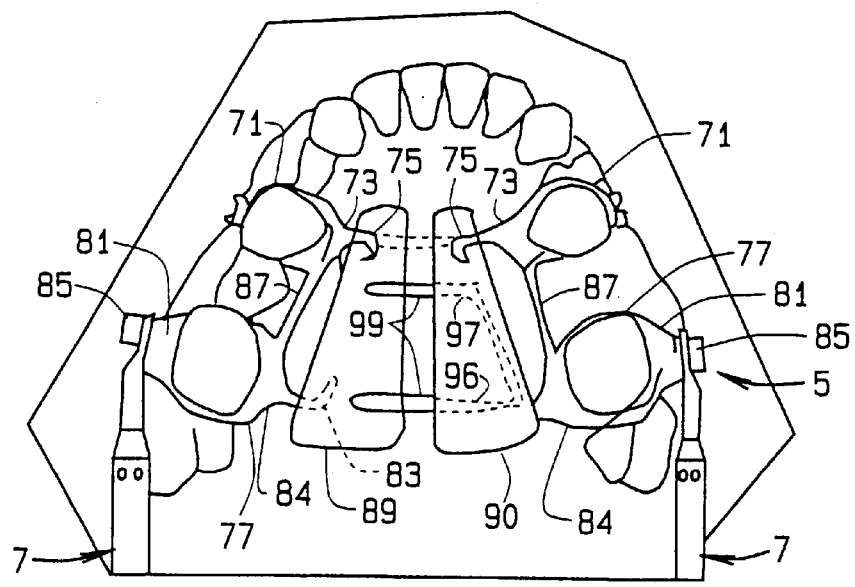
FIG. 1A is a bottom plan view of the maxillary arch expander mounted in the mold with the telescoping assembly mounted thereto.
Figure 1B:
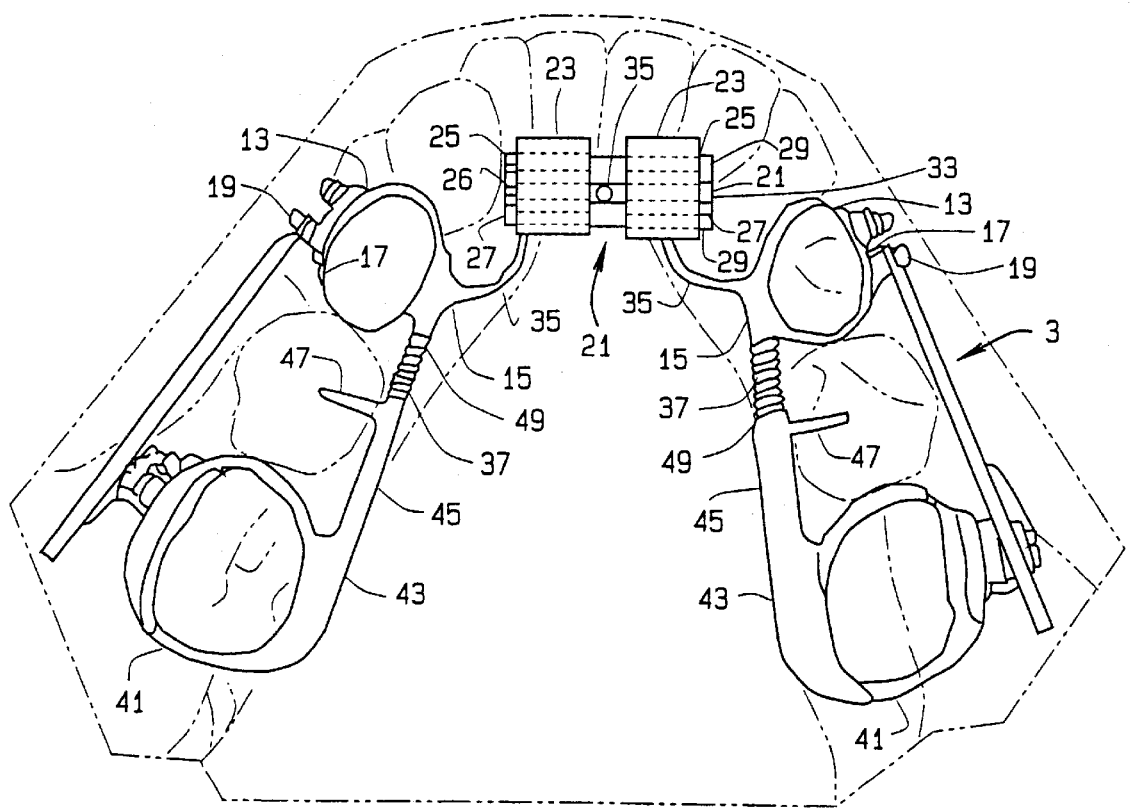
FIG. 1B is a top plan view of the mandibular arch expander mounted in the mold with the telescoping assembly mounted thereto.

Turning initially to FIGS. 1–1B, an orthodontic appliance 1 of the present invention is shown mounted in a mold M of a mouth. Although the appliance 1 is shown mounted in a mold, it will be appreciated that it is designed for use in a human mouth to increase the size of a child's mouth so that the child's permanent teeth will not be crowded when they erupt. This will reduce the need for extractions of permanent teeth. The appliance I includes a mandibular arch expander 3, a maxillary arch expander 5, and a pair of telescoping assemblies 7 which extend between and connect the mandibular and maxillary arch expanders 3 and 5, as described below.

The mandibular and maxillary arch expanders 3 and 5 are substantially the same as the arch expanders set forth in my above noted U.S. Pat. No. 5,645,422, which is incorporated herein by reference. The mandibular arch expander 3 (FIG. 1B) has a pair of spaced apart forward orthodontic bands 13 which are adapted to attach to the mandibular first primary molars. Bands 13 each have a boss 15 positioned on the lingual side of the bands and a boss 17 positioned on the buccal side of the bands. The buccal bosses 17 are adapted to receive screws 19 to connect the telescoping assemblies 7 to the mandibular arch expander 3, as will be discussed below. The respective bosses 15 and 17 are integrally formed on the respective bands to provide a substantial metallic body for the attachment of other elements to be described hereinafter.

The bands 13 are interconnected by an expansion complex 21. The expansion complex 21 has a pair of metal blocks 23. The blocks 23 each have three bores 25, 26, and 27 formed laterally therethrough. The bores 25, 26, and 27 of the two blocks 23 are in substantial horizontal alignment. Aligning pins 29 extend through the outer bores 25 and 27. The respective aligning pins 29 are slightly undersized relative to the respective bores 25 and 27 so that the blocks 23 will slide relative to the pins 29. The middle bores 26 are threaded and receive a threaded screw 33. There is at least one hole 35 formed through the middle of screw 33 between the oppositely threaded ends. The hole 35 accommodates the insertion of a small tool to turn screw 33. It will be appreciated that threaded screw 33 has oppositely threaded ends. Therefore, when screw 33 is rotated in one direction, the blocks 23 are moved away from each other and when screw 33 is rotated in the opposite direction, the blocks 23 are drawn toward each other. The blocks 23 slide on the aligning pins 29 and the aligning pins serve to stabilize the expansion screw complex.

The blocks 23 are mounted to the lingual bosses 15 by curved arms 35 which extend between the bosses 15 and the block 23. The curved arms 35 can be of any appropriate length and curvature to suitably engage the patient's teeth. The mold M is made following conventional procedures and the arms 35 are fabricated to be the appropriate length and curvature. The arms 35 then are soldered to the appropriate boss 15 and to the expansion screw complex 21.

A rod 37 extends rearwardly from each of the lingual bosses 15. The rod 37 can be a small hollow tube, to reduce weight, or can be a solid rod. A stated above, the exact position on the respective bosses 15 where the rods 37 are attached and the angle at which the rod 37 extends from the bosses 15 depends upon the patient and the patient's needs. It will be appreciated that arms 35 and rods 37 can be one integral piece appropriately bent to form the arm and the rod, or the arm and rod can be separate pieces.

The mandibular arch expander 3 also has a pair of spaced apart rear orthodontic bands 41. The bands 41 generally are molar bands and, in use, are attached to the permanent first molars. Each band 41 has an integral boss 43 positioned on the lingual side of the bands. A hollow tube 45 extends forwardly from each boss 43. The hollow tubes 45 have an internal bore sized to accommodate the sliding insertion of the rods 37, as will be explained in detail below.

A pair of short wires 47 extend perpendicularly from the tubes 45. The respective short wires 47 extend buccally and serve as occlusal rests and are soldered on the respective tubes at a position corresponding to the lingual occlusal groove of the deciduous second molars bilaterally to provide extra support and stability to the tubes.

The forward pair of orthodontic bands 13 are connected to the rear pair of orthodontic bands 41 to promote molar distalization and added archlength development by a pair of spring-loaded rod and tube assemblies. Rods 37 are slidingly engaged in tubes 45. Coil springs 49 are positioned around rod 37 and fixed between bosses 15 and the end of the tube 45. The coil springs 49 are sized so they abut the ends of the tubes 45 and do not slide over the tubes 45. The respective coil springs 49, therefore, urge the forward bands 13 away from the rear bands 41 to increase palate length.

The coil springs 49 have a preset tension. The preset tension of the spring is selected by the orthodontist to effect the appropriate mesial distal archlength development in the bicuspid area.

Figure 1C:
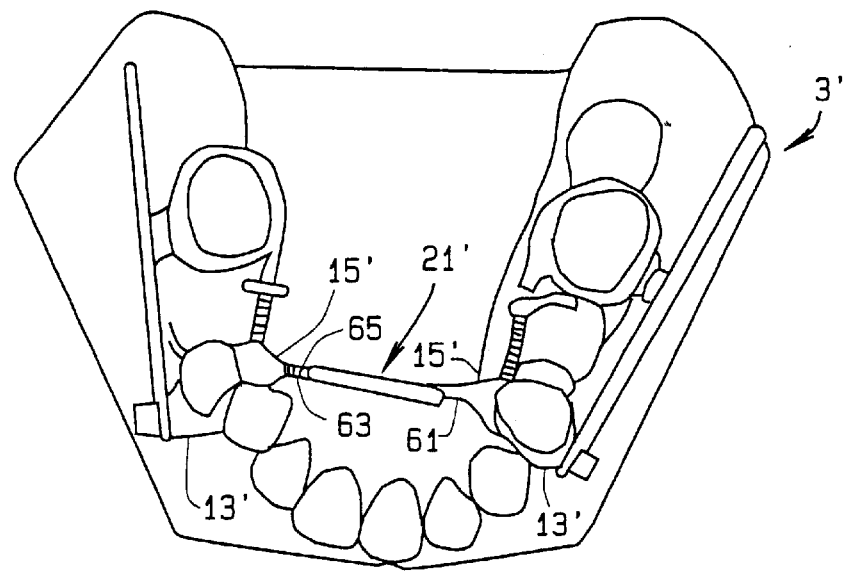
FIG. 1C is a top plan view similar to that of FIG. 1B, but with an alternative mandibular arch expander.

An alternative embodiment of the mandibular arch expander 3' of the present invention is shown in FIG. 1C. The mandibular arch expander 3' is substantially identical to the mandibular arch expander 3 shown in FIG. 1B. It varies, however, in the construction of the expansion complex 21'. The arch expander 3' includes spaced apart forward orthodontic bands 13' having lingual bosses 15'. The expansion complex 21' includes a hollow tube 61 extending from one boss 15' and a rod 63 extending from the other boss 15'. The angles at which the tube 61 and rod 63 extend from the respective bosses depends upon the shape of the patient's mouth. The rod 63 is slidingly engaged in the tube 61. A coil spring 65 is journaled around the rod 63 and fixed between the boss 15' and the end of the tube 61. The spring 65 is sized to engage the end of the tube 61 and not slip over the tube 61. Therefore, the spring 65 urges the forward bands 13' away from each other. The spring 65 has a predetermined force to be delivered between the molars to widen the anterior canine width.

The maxillary palatal expander 5 (FIG. 1A) has a pair of spaced apart forward orthodontic bands 71 which are adapted to attach to the maxillary molars. The each band 71 has a boss 73 positioned on the lingual side of the bands. The respective bosses are integrally formed on the respective bands. There is an integral curved member or hook 75 extending inwardly or lingually from the bosses 73.

A pair of spaced apart rear orthodontic bands 77 are positioned rearwardly of the forward bands 71. The bands 77 each have an integral lingual boss 79 and an integral buccal boss 81. The lingual bosses 79 have an integral curved member or hook 83. The buccal bosses 81 each have a screw hole to revive a screw 85 to connect the telescoping tube assemblies 7 to the maxillary arch expander 5.

The forward orthodontic bands 71 are connected to the rear orthodontic bands 77 by a rod 87. Furthermore, the hooks 75 and 83 are embedded in plastic plates 89 and 90. The respective plastic plates are molded to fit the patient's palate. Each plate, with the associated forward and rearward bands, comprises half of the expander 5. The halves of the expander 5 are biased away from each other to widen the maxillary arch. There is a substantially U-shaped rod 91 imbedded in plate 90. The rod 91 has legs which extend out from, and at substantially right angles to, the plastic plate 90. Coil springs 96 and 97 are journaled around the legs of the rod, respectively. A pair of short tubes 99 are embedded in the plate 89. The tubes 99 extend out of the palate plate 89 at substantially right angles to the palate plate. The tubes 99 are on complementary alignment with the legs of the U-shaped rod 91 and are slightly oversized so that the legs can slide into the tubes. The springs 96 and 97 abut the ends of the tubes 99 and exert tension force to urge the halves of the appliance apart. The appropriate tension can be exerted by selecting springs with the appropriate tension. The mandibular expander 3 of FIG. 1B can be modified to replace its expansion complex 21 with the plates 89 and 90 of FIG. A, and to include the structure associated with the plates 89 and 90.

To facilitate transverse development of the lower jaw relative to the upper jaw, the maxillary and mandibular arch expanders are interconnected by the telescoping Herbst-type assemblies 7, which are shown in detail in FIGS. 2–10. The two assemblies are identical and include a posterior tube 101, an anterior tube 103, and a rod 105 which extends through the two tubes 101 and 103. The posterior tube 101 includes a hollow body 107 which is open at both its front and back ends. The body 107 has an outer diameter which is substantially constant between its front and back ends.

The back end 109 is externally threaded, as at 111. An arm 113 extends upwardly from the tube's body 107 at the front 115 of the body. The arm 113 has an eyelet 117 at its free end, the eyelet having a hole 119 therein. Intermediate its front and back ends, the posterior tube 101 includes a plurality of tick marks 121 which are used to indicate the amount of advancement of the anterior tube 103 over the posterior tube 101, as will be described below. The tick marks 121 are preferably separated by about one millimeter.

The anterior tube 103 includes a hollow body 123 defining a bore 125 therethrough. The tube 103 is open at both its back and front ends 127 and 129, respectively. The front end 127 of the tube tapers inwardly, as at 131 such that the very front of the tube 103 has a smaller outer diameter than the rest of the tube's body 123. As seen in FIGS. 8 and 10, the body 123 also tapers slightly from the back of the surface 131 to the back 129 of the body 123. The tube 123 is internally threaded at its front end, as at 133. The diameter of the bore 125 is slightly greater than the outer diameter of the anterior tube 101, and the threads 111 and 133 of the tubes 101 and 103, respectively, are machined or otherwise formed so that they will mate. Thus, the anterior and posterior tubes 101 and 103 are threadedly connected together. Notches or holes 135 are formed on the exterior of the posterior tube body 123. The notches 125 are adapted to receive a tool having a correspondingly shaped head. The tool can be used to rotate the posterior tube 103 relative to the anterior tube 101 when the appliance 1 is mounted in a patient's mouth.

The rod 105 is a generally straight rod. It has a generally constant diameter slightly greater than the inner diameter of the anterior tube 101, so that it may slide relative to the tube 101. At its back end, the rod 105 has an eyelet 141 having a hole 143.

The telescoping tube assemblies 7 are assembled by threadedly connecting the anterior and posterior tubes 101 and 103, and sliding the rod 105 into the tube assembly. The rod 105 is slid into the tube assembly such that its eyelet 141 will be at the opposite end of the assembly from the anterior tube eyelet 117.

As best seen in FIG. 1, the tube assemblies 7 extend between the forward bands 13 on the mandibular arch expander 3 and the rear bands 77 on the maxillary arch expander 5. The screws 85 of the maxillary arch expander pass through the eyelet's 117 of the anterior tubes 101 to pivotally connect the tube assembly to the maxillary arch expander. Similarly, the screws 19 of the mandibular arch expander 3 pass through the eyelets 141 of the rod 105 to connect the assembly 7 to the mandibular arch expander 3.

When initially inserted in a patient's mouth, the telescoping tube assemblies 7 are sized such that the back end 129 of the posterior tube 103 is in contact with the eyelet 141 of the rod 105 when the patient's mouth is shut. This will apply a forwardly directed pressure on the mandible. Thus, with all the components (i.e., the mandibular and maxillary arch expanders 3 and 5, and the telescoping tube assemblies 7 and 8) installed in a patient's mount, the appliance 1 will allow for transverse development, archlength development, palatal expansion and mandibular advancement, simultaneously without requiring patient compliance.

By rotating the tube 103 in one direction, the tube 103 will advance over the tube 101, to shorten the overall length of the tube assembly 7. Conversely, by rotating the tube 103 in a second direction, the tube 103 will be retracted relative to the anterior tube, to increase the overall length of the tube assembly. The extent of the movement of the tubes 101 and 103 relative to each other is measured by the tick marks 121. The interior threads 33 of the tube 103 and the tick marks 121 of the tube 101 are positioned on their respective tubes, such that when the tube 101 is threaded into the tube 103, the tick marks 121 will be exposed. By rotating the two tubes relative to each other, the number of tick marks exposed increases or decreases, depending on the direction of rotation, to indicate how far the tube assembly has been lengthened or shortened by the rotation of the tubes relative to each other. Thus, by reading the number of tick marks exposed, the practitioner can determine the amount of advancement that has occurred, as well as the overall length of the assembly 7.

Figure 1D:
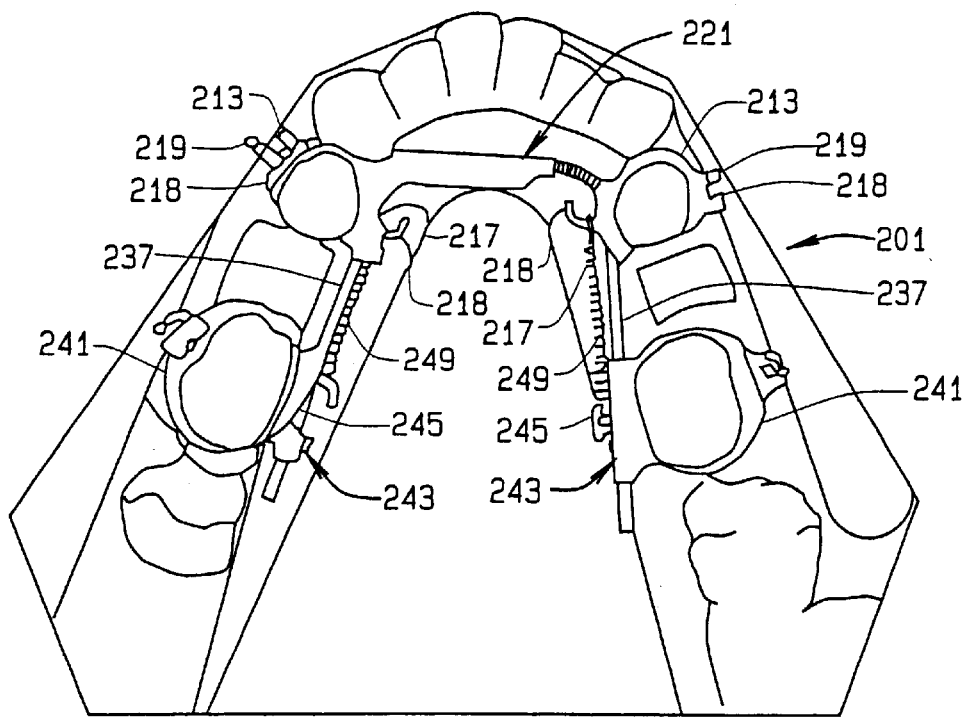
FIG. 1D is a top plan view of a mandibular molar space closer which can be used with the telescoping assembly.

A mandibular molar space closer 201 is shown in FIG. 1D. As can be seen, it is similar to the mandibular arch expander of FIG. 1C. The molar space closer 201 has a pair of spaced apart forward orthodontic bands 213 which are adapted to attach to the mandibular first primary molars. The bands 213 each have a boss 215 positioned on the lingual side of the bands and a boss 217 positioned on the buccal side of the bands. The buccal bosses 217 are adapted to receive screws 219 to connect the telescoping assemblies 7 to the mandibular arch expander 3. The respective bosses 215 and 217 are integrally formed on the respective bands to provide a substantial metallic body for the attachment of other elements to be described hereinafter. A hook 218 extends from the buccal boss 217 and points forwardly, toward the front of the patients mouth.

The bands 213 are interconnected by an expansion complex 221. The expansion complex 221 which is identical to the expansion complex 21' of the mandibular arch expander 3'.

A rod 237 extends rearwardly from each of the lingual bosses 217. The rod 237 can be a small hollow tube, to reduce weight, or can be a solid rod. A stated above, the exact position on the respective bosses 217 where the rods 237 are attached and the angle at which the rod 237 extends from the bosses 217 depends upon the patient and the patient's needs.

The mandibular molar space closer 201 also has a pair of spaced apart rear orthodontic bands 241. The bands 241 generally are molar bands and, in use, are attached to the permanent first molars. Each band 241 has an integral boss 243 positioned on the lingual side of the bands. A hollow tube 245 extends along the lingual side of the band and through the boss 243. The hollow tubes 245 have an internal bore sized to accommodate the sliding insertion of the rods 237. The rods 237 sized such that they will pass through the tubes 245 to extend beyond the rear of the tubes 245.

The forward pair of orthodontic bands 213 are connected to the rear pair of orthodontic bands 241 to reduce the spacing between molars using a pair of spring-loaded rod and tube assemblies. Rods 237 are slidingly engaged in tubes 245, as noted. Coil springs 249 are connected to the rod 237 behind the rear molar band 241 and to the hooks 217. As seen, in this position, the springs 249 are in an expanded state. The respective coil springs 249, therefore, pull the bands 213 and 241 towards each other to decrease the spacing between molars. The coil springs 249 have a preset tension. The preset tension of the spring is selected by the orthodontist to effect the appropriate mesial distal archlength development in the bicuspid area.

Figure 11:
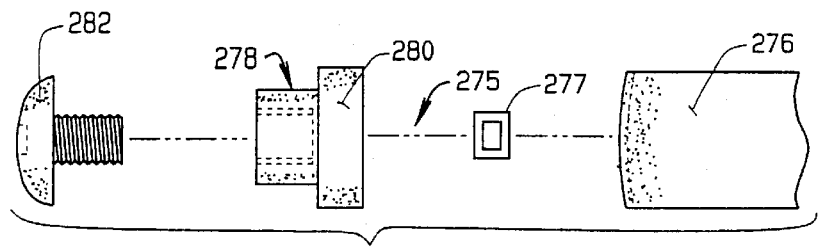
FIG. 11 is an exploded view of a prior art pivotal mounting boss assembly and an orthodontic band with a rectangular tube interposed to accommodate an arch wire.
Figure 12:
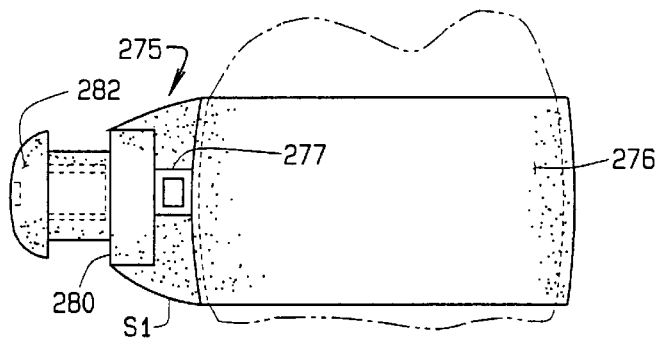
FIG. 12 is a perspective view of the prior art pivotal mounting boss assembly of FIG. 11 attached to an orthodontic band with a rectangular tube interposed to accommodate an arch wire.

A prior art mounting boss assembly gerry-rigged to accommodate an arch wire W is shown in detail in FIGS. 11 and 12 and indicated generally by reference numeral 275 shown in use with an orthodontic band 276. It will be appreciated that assembly 275 is described as attached to an orthodontic band but can be attached to a stainless steel crown as well Assembly 275 functions as the above described bosses attached to the orthodontic bands. However, assembly 275 is modified to allow the attachment of arch wires. The prior art assembly 275 includes a short segment of square tubing 277 which is attached to the band 276 by soldering, as at S1, for example. The square tubing is positioned on the orthodontic band for the attachment of an arch wire W, if needed. A mounting boss 278 including a base casing 280 and a screw 282 is then soldered on top of the square tubing. It will be appreciated by those skilled in the art that the prior art assembly 275 requires a substantial solder joint S1 to secure the elements which results in a high profile boss. Moreover, installation of the boss on the band requires addition time and costs.

Figure 13:
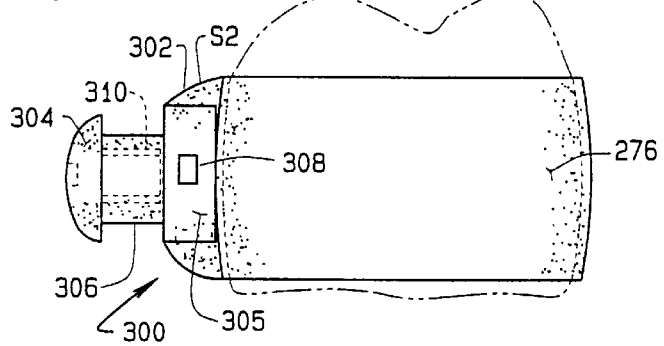
FIG. 13 is a perspective view of the improved pivotal mounting boss assembly of the present invention attached to an orthodontic band.
Figure 14:
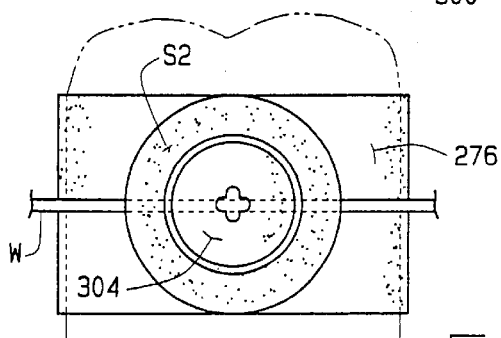
FIG. 14 is a top plan view of the improved pivotal mounting boss assembly.

An improved pivotal mounting boss is illustrated in FIG. 13 and shown in application in FIGS. 1, 1C and 2 is indicated generally by reference numeral 300. Mounting boss 300 includes a base casing 302 and a threaded screw 304. Base casing 302 includes a generally cylindrical base segment 305 and a concentric cylindrical body segment 306. Base segment 305 has an opening 308 formed therein. In the illustrated embodiment opening 308 is rectangular and is designed to accommodate a conventional arch wire W. See FIG. 14. The base segment 304 can be positioned on the orthodontic band 276 and soldered in place with solder S2. It will be appreciated that the opening 308 can be positioned at a predetermined angle as desired by the orthodontist for root angulation. It will be appreciated that less solder S2 is required to attach the mounting boss 300 to the orthodontic band resulting in less bulk and a lower profile arrangement than that shown in FIG. 12.

The body segment 306 includes an internally threaded bore 310 for the threaded engagement of screw 304 The screw 304 is inserted through the eyelet of the orthodontic device described above and tightened, leaving enough clearance so that the eyelet can rotate or pivot about the screw.

Another mandibular arch expander 401 is shown in FIG. 15. Although the expander 401 is shown embodied in a mandibular arch expander. It will be apparent that it can also be embodied in a maxillary arch expander. The expander 401 is substantially similar to the expander 3 of FIG. 1B. The mandibular arch expander 401 has a pair of spaced apart forward orthodontic bands 413 which are adapted to attach to the mandibular first primary molars. The bands 413 each have a boss 415 positioned on the lingual side of the bands and a boss 417 positioned on the buccal side of the bands. The buccal bosses 417 are adapted to receive screws 419 to connect the telescoping assemblies to the mandibular arch expander.

A rod 437 extends rearwardly from each of the lingual bosses 415. The rod 437 can be a small hollow tube, to reduce weight, or can be a solid rod. A stated above, the exact position on the respective bosses 415 where the rods 437 are attached and the angle at which the rod 437 extends from the bosses 415 depends upon the patient and the patient's needs.

The mandibular arch expander 401 also has a pair of spaced apart rear orthodontic bands 421. The bands 421 generally are molar bands and, in use, are attached to the permanent first molars. Each band 421 has an integral boss 423 positioned on the lingual side of the bands. A hollow tube 425 extends forwardly from each boss 423. The hollow tubes 425 have an internal bore sized to accommodate the sliding insertion of rods 437 which extend rearwardly from the forward orthodontic bands 413. Springs 429 are mounted on the rods 427 to apply a pressure to the forward orthodontic band, as discussed above. It will be appreciated that arms 429 and rods 437 can be one integral piece appropriately bent to form the arm and the rod, or the arm and rod can be separate pieces.

The difference between the mandibular arch expanders 3 and 401 lie in the expansion complexes of the two expanders. The expansion complex 441 uses an advancing sheath design which is similar to the sliding element 7 of FIGS. 2–10. The expander assembly is shown on an enlarged scale in FIG. 16. It includes a body 443 and a rod 445. The body 443 is hollow and defines a passageway 447 through the body. The passageway is open at its back end 449 and its front end 451. The body 403 is internally threaded, as at 452. The threads 453 are shown to be spaced rearwardly of the front end 451 of the passageway 447. However, the threads can extend throughout as much or as little of the body passageway as desired.

An arm 453 is received in the back end 449 of the passageway 447 and extends through the body 443 and out the front end 451 of the body 443. The arm 453 extends from the lingual boss 415 of one of the forward molar bands 413. The arm 453 and body boss 447 are sized so that the body 443 can rotate about the arm 453.

The rod 445 is sized to fit within the body passageway 447. A rear portion 461 of the rod 445 is externally threaded, so that the rod can be screwed into the body 403. At least a portion of the rod 445 is hollow, defining a bore 462 which extends forwardly from the back end of the rod 445. The bore 462 is sized to telescopically receive the forward end of the arm 453. A plurality of tick marks 463 are formed on the rod 445 forwardly of the threads. As with the assembly 7, the tick marks 463 enable the practitioner to know how far the rod 445 is extending from the body 403. The forward end 465 of the rod 445 is soldered, or otherwise fixed to, the lingual side of the other forward orthodontic band 413.

Thus, the rod 445 is effectively fixed to one of the forward orthodontic bands and the body 443 is effectively rotationally mounted to the other of the forward orthodontic bands. As seen in FIG. 15, the back end 449 of the body 443 is in abutting contact with the band 413 to which the arm 453 is mounted. Therefore, by rotating the body 443 relative to the rod 445, the overall length of the expansion complex can be selectively increased over time to increase the width of a patients jaw. Using the tick marks 463 on the rod 445, the dentist or technician can determine the overall length of the expansion complex, and can thus monitor the patient's progress.

Figure 17:
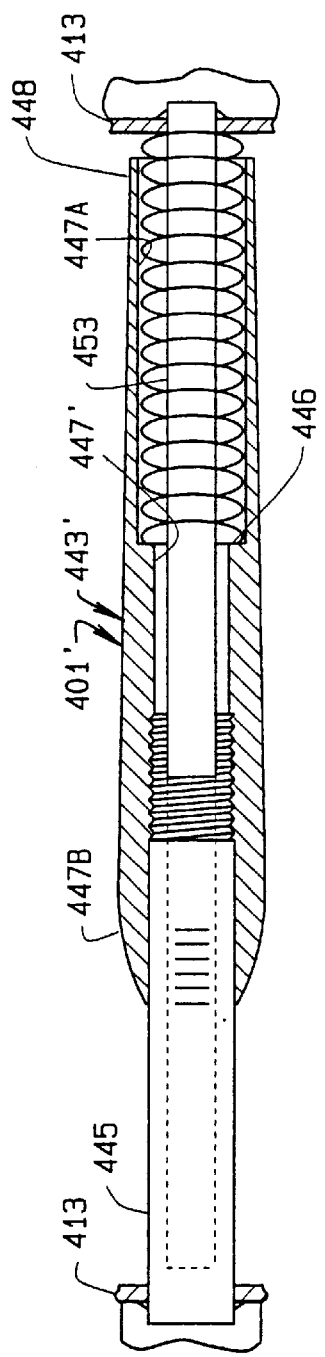
FIG. 17 is a cross-sectional view of the telescoping assembly of FIG. 16 wherein the telescoping assembly is provided with a coiled spring.

A modified expansion complex 401' is shown in FIG. 17. The expansion complex 401' is substantially identical to the expansion complex 401 of FIG. 15, and includes the rod 445 and arm 453. The difference is that the passage 447' of the body 443' is counterbored, as at 447A, to effectively produce a passage of two different diameters, the passage having a larger diameter in the back portion 447A than in the front portion 447B, with a shoulder 446 at the transition between the two sections. A coiled spring 448 is received in the counterbored portion 447A of the passage 447' and is coiled about the arm 453. The spring 448 is preferably a nickel-titanium spring and is sandwiched between the molar band 413 to which the arm 453 is mounted and the shoulder 446. The advantage of the spring 448 is that it will apply a constant pressure to the mandible to expand the mandible. Further, the expansion force comes from the spring, rather than from the back edge of the body 443. However, adjustments would still be made by rotating the body 443. The passage 447 in the body 443 (FIGS. 15 and 16) need not extend all the way through the body 443. The body could have a rear bore which accepts the arm 453 and a forward internally threaded bore which excepts the rod 445. This example is merely illustrative.

Figure 18:
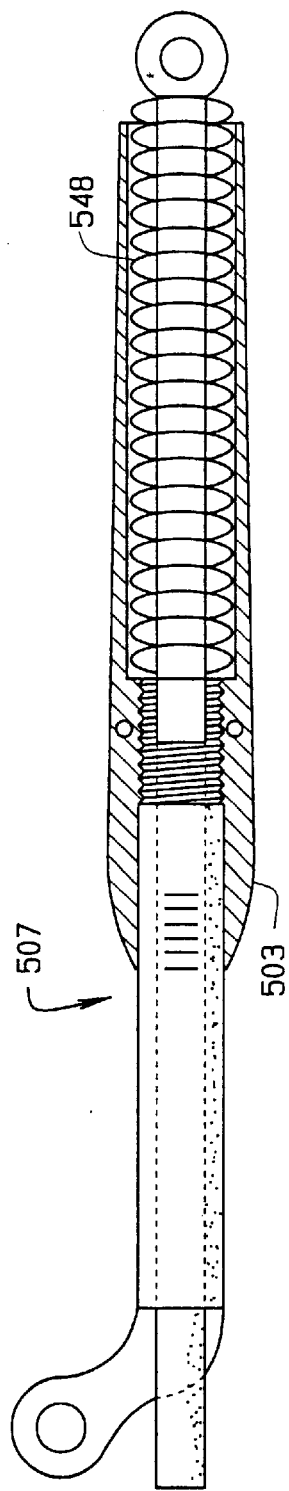
FIG. 18 is a cross-sectional view of a telescoping assembly similar to FIG. 2, but adapted to include a coiled spring.

FIG. 18 shows a telescoping assembly 507 similar to the assembly 7 if FIG. 2. However, the assembly 507 has been modified to include a spring 548 in the body 503, similarly to the telescoping assembly 441 of FIG. 17.

Although the foregoing designs work well in most treatments, the inventor has determined that there can be some molar crown tipping in the transverse dimension analysis. To correct that problem, the inventor has developed modifications to the design that feature tubes having cylindrical outer configuration with an inner lumen that has flat sides. The rod which seats in the lumen has a complementary configuration. This design resists the turning or rotation of the rod within the tube which can result in molar crown tipping during treatment. The new designs are best illustrated in FIGS. 19–27.

FIGS. 19–21 illustrate one embodiment of the modified tube and rod indicated by reference numerals 600 and 601 respectively. As will be appreciated, the gross structure of the modified tube and rod are similar to those described above. However, as best seen in FIGS. 20 and 21, the rod 600 has a rectangular cross section. Tube 601 has a complementary rectangular bore 603, which is slightly oversized relative to tube 601 to allow the introduction of rod 600 into bore 603. As will be appreciated, the rectangular shapes of the bore and rod prevent the rod from turning or rotating within the tube to retard molar tipping in use.

FIGS. 22–24 illustrate another embodiment of a modified tube and rod indicated by reference numerals 700 and 701 respectively. As will be appreciated, the gross structure of the modified tube and rod are similar to those described above. However, as best seen in FIGS. 23 and 24, the rod 700 has an ovoid cross section. Tube 701 has a complementary ovoid bore 703, which is slightly oversized relative to tube 701 to allow the introduction of rod 700 into bore 703. As will be appreciated, the ovoid shapes of the bore and rod also prevent the rod from turning or rotating within the tube to retard molar tipping in use.

FIGS. 25–27 illustrate another embodiment of the modified tube and rod indicated by reference numerals 800 and 801 respectively. As best seen in FIGS. 26 and 27, the rod 800 has a substantially rectangular cross section with rounded top and bottom outer walls 802A and 802B, respectively. Tube 801 has a complementary substantially rectangular bore 803, having an arced or rounded top wall 804A and rounded bottom wall 804B which is slightly oversized relative to tube 601 to allow the introduction of rod 800 into bore 803. The rounded walls on the tube and rod facilitate ease of movement for adjustment; the flat side walls facilitate soldering and prevent the rod from turning or rotating within the tube to retard molar tipping.

The designs shown in FIGS. 22–27 can be employed in any of the previously described and illustrated expanders. The designs of FIGS. 22–27 can be used to replace rod 37 and tube 45 as shown in FIG. 1B. Likewise the embodiments of FIGS. 22–27 can be incorporated in the expander shown in FIG. 1D in place of rod 237 and tube 245. The present invention contemplates the use of a rod and tube assembly that resists twisting or rotation in any expander that uses a novel rod and tube assembly. It will be appreciated that the illustrated designs that resist twisting or rotation are intended to be usable in any orthodontic expander that includes at least one rod and tube assembly.

Figure 28:
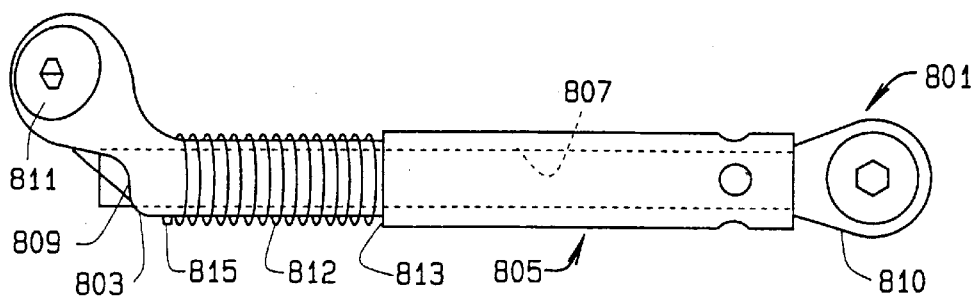
FIG. 28 is a side elevational view of another embodiment of the telescoping assembly which compensates for jaw pressure which can cause the telescoping assembly to thread backwards.

The inventor has also found that with respect to the advancing sheath, the jaw pressure to return to a retruded chin position may cause the adjustable tube of the advancing sheath to thread backwards after it has been advanced. A modified advancing sheath is shown in FIG. 28. The advancing sheath 801 includes a hollow posterior tube 803, a hollow anterior tube 805, and a rod 807 which extends through the two tubes 803 and 805. The posterior tube 803 is externally threaded at its back end. The anterior tube 805 is internally threaded to be threaded onto the back end of the posterior tube to facilitate adjustment of the overall length of the sheath through which the rod 807 extends. An arm 809 extends upwardly from the posterior tube's forward end. An attachment 811 is formed at the free end of the arm to connect the tube to a tooth band. A second attachment 810 is formed on the back end of the rod 807. A spring 812, preferably a coil spring made from a nickel titanium, is journaled about the posterior tube 803 between the forward end 813 of the anterior tube 805 and the arm 809 of the posterior tube 803. A stop 815 is provided just behind the arm 809 to form a forward stop for the spring 812. The spring 812 will place a constant forward pressure on the advancing or posterior tube 805 to assist it in resisting the tendency for the tube 805 to back up under constant retrusive jaw pressure.

Figure 29:
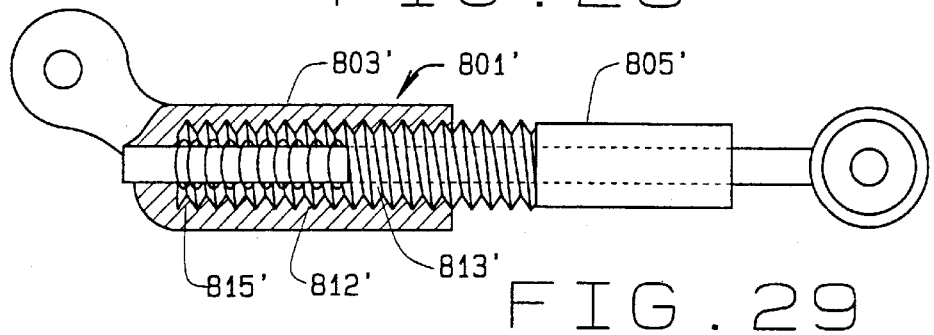
FIG. 29 is a side elevational view, partly in cross-section, of an alternative embodiment of the telescoping assembly of FIG. 28.
Figure 30:
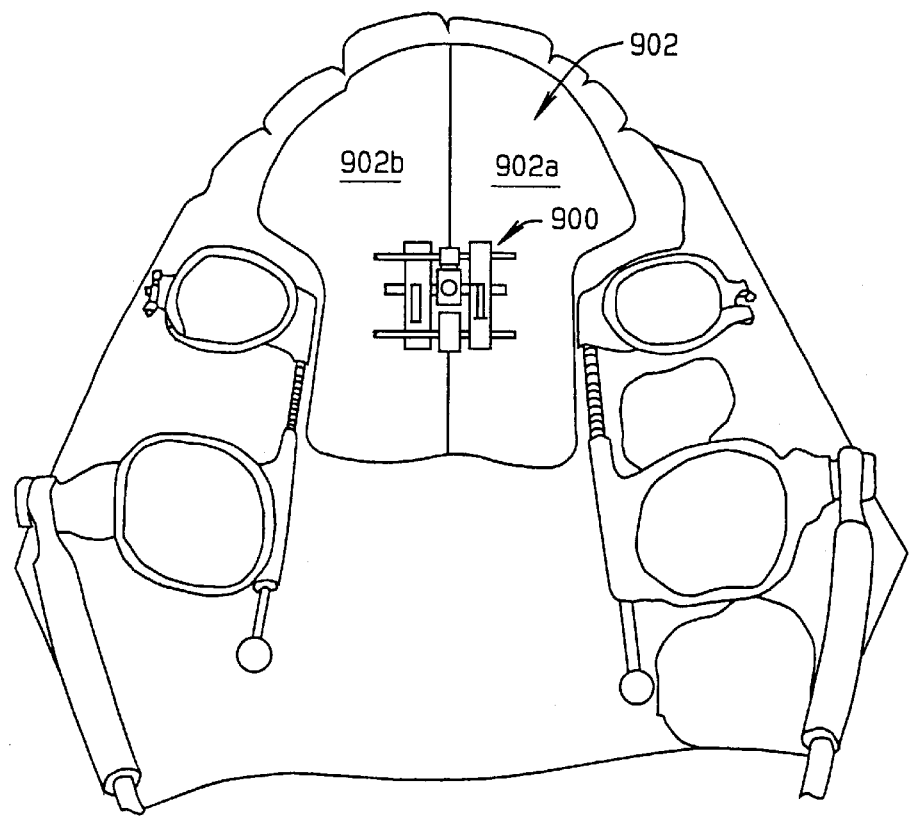
FIG. 30 is a plan view of a further embodiment of a maxillary arch expander encased in plastic and mounted in a patient's mouth.

A variation of the advancing sheath 801 is shown in FIG. 29. In the advancing sheath 801', the posterior tube 803' is internally threaded and the anterior tube 805' is externally threaded. In this variation, the spring 812' is received within the tube 803' between a forward end 815' in the tube 803' and a forward end 813' of the anterior tube 805'.

Figure 32:
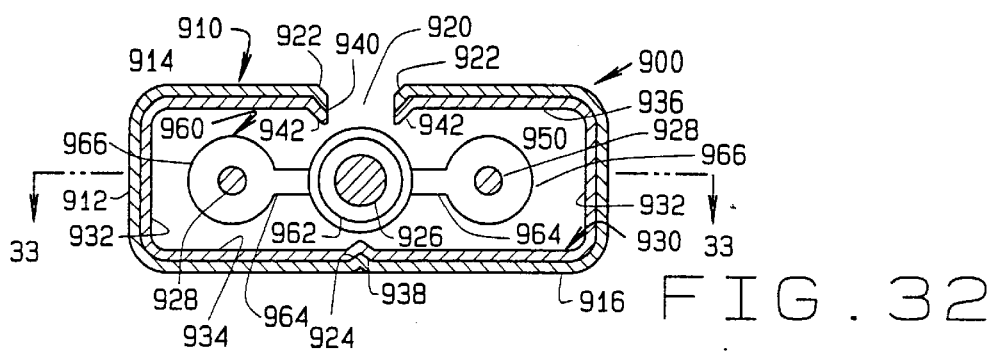
FIG. 32 is a cross-sectional view of the arch expander taken along line 32—32 of FIG. 31.
Figure 31:
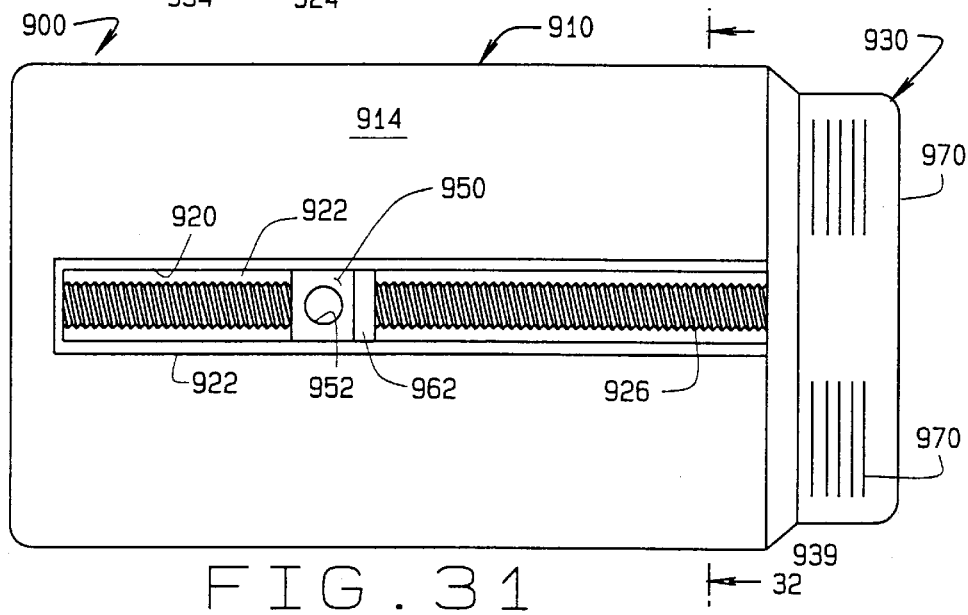
FIG. 31 is a plan view of the arch expander.
Figure 33:
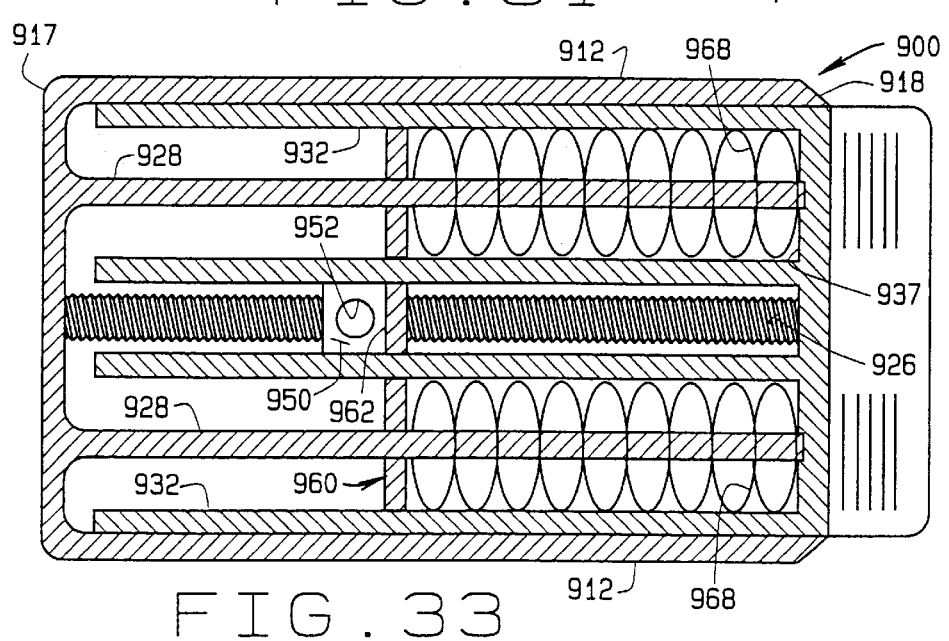
FIG. 33 is a cross-sectional view of the arch expander taken along line 33—33 of FIG. 32.

In FIGS. 30–33, an alternative expansion mechanism 900 is shown. The expansion mechanism 900 is encased in a plate 902 having halves 902a and 902b which are sized and shaped to fit against a patient's mandibular or maxillary arch. The expansion mechanism 900 includes an outer housing 910 having side walls 912, a top 914, a bottom 916, a back 917, and an open front 918. A channel or groove 920 extends rearwardly from the front edge 918 of the outer housing 910. The groove 920 is defined by sloped walls 922 on opposing sides of the channel. Thus, as seen in FIG. 32, the bottom of the sloped wall 922 is below the inner surface of the rest of the top 914. A triangular shaped rib 924 runs along the center of the inner surface of the bottom 916 between the back 917 and the front 918. A threaded rod 926 extends forwardly from the housing back wall 917 to the front 918. The threaded rod 926 extends along the center of the housing, and is generally above the rib 926. A pair of posts 928 are disposed on opposite sides of the threaded rod 926, and, like the rod 926, extend forwardly from the back wall 917 to the front wall 918.

An advancing member 930 is slidably received in the housing 910. The member 930 has side walls 932, a bottom 934, a top 936, and a front wall 937. A forward mounting portion 939 extends from the front wall 937. A groove 938 is formed on the outer surface of the bottom 934 and is sized and shaped to slide on the rib 924 of the housing 910. Additionally, a channel 940 having sloped walls 942 is formed in the top 936. The channel 940 is aligned with the housing channel 920, and the sloped walls 942 are complimentarily shaped to the housing's sloped walls 922. Thus, the interaction of the groove 938 with the rib 924 and of the sloped walls 922 and 942 surrounding the channels 920 and 940, respectively, act as keys or guides for the member 930 as it is moved, as will be discussed below.

An internally threaded activation nut 950 is received on the housing's threaded rod 926. The nut 950 is sized such that its peripheral edge is accessible through the channels 920 and 940. The nut 950 includes a plurality of holes 952 in its periphery. The holes 952 are accessible through the channels 920 and 940 using a tool to rotate the nut 950. As can be appreciated, by rotating the nut 950, the nut 950 will move along the rod 926.

An activation wing 960 is mounted in the housing 910 in front of the activation nut 950 to be moved by the nut. The wing 960 includes a central portion 962 which is journaled about the threaded rod 926. The central portion 962 has a central opening sized to prevent the threads of the rod 926 from interfering with movement of the activation wing 960. A pair of arms 964 extend from opposite sides of the central portion 962, and a plate 966 is on the distal end of each arm 964. The plates 966 each have a central hole sized to be received on the posts 928. A spring 968 is journaled around each post 928 between the plates 966 and the front wall 937 of the movable member 930.

As can be appreciated, by rotating the nut 950 such that it moves toward the movable member front wall 937, the activation wing 960 will be moved forwardly, and the springs 968 will be compressed. The springs 968 will thus apply a pressure against the moveable member 930 to cause the housing 910 and the moveable member 930 to move relative to each other, thereby causing expansion of the member 900. Preferably, the moveable member 930 is provided with markings 970, such as millimeter markings so that it can be determined how far the moveable member 930 has been advanced. The markings 970 are preferably provided on the mounting portion 939 of the advancing member 930. When the expansion complex 900 is fixed in the plates 902*a* and *b*, the housing 910 is fixed in one of the plates, such as plate 902*a*, and the advancing member 930 is mounted in the other of the plates, such as plate 902*b*. The housing 910 can be effectively seated in an appropriately sized and shaped opening in the plate 902*a*. The advancing member 930 is mounted to the plate 902*b* using the mounting portion 939. The mounting portion 939 is received in a groove or opening at an inner edge of the plate 902*b*. When the two halves of the expansion complex are fixed in their respective plate halves, the channels 920 and 940 will be accessible, and the markings 970 will be visible. The outer surfaces of the housing 910 and the advancing member 930 which are fixed to the plates 902*a,b*, can have roughened surfaces to facilitate permanent attachment of the housing 910 and advancing member 930 to their respective plates 902*a,b*.

The rib 924 and groove 938 are shown to be triangular, the rib and groove could be any other desired shape. More than one rib and groove could be provided. Additionally, the rib and groove could be reversed, such that the rib is on the advancing member 930 and the groove is on the housing 910.

FIGS. 34A through 38 illustrate a contraction sheath connector used to treat underbite, particularly Class III malocclusion. The contraction sheath connector of the present invention, for example the embodiment of the connector indicated generally by reference numeral 1000 in the drawings, is connected between a maxillary molar or a maxillary appliance and a mandibular appliance. When the mandibular appliance is connected to the maxilla by a contraction sheath connector, the connector forces the mandibular appliance to distalize the mandibular molars and retards any forward development of the malocclusion underbite, while resisting any reciprocal molar distalization in the maxillary arch as it forces the maxilla to advance. It will be understood that the novel contraction sheath connector of the present invention may be employed with an appliance such as a molar band or one of the other maxillary appliances and one of the mandibular appliances described above.

Figure 34A:
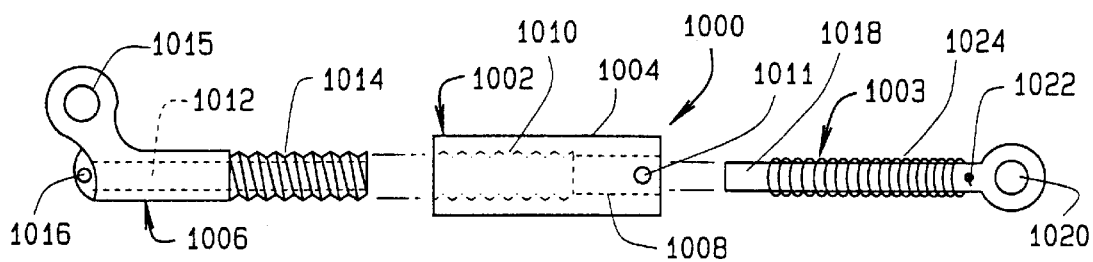
FIG. 34A is an exploded view of a novel contraction sheath connector of the present invention.
Figure 34B:
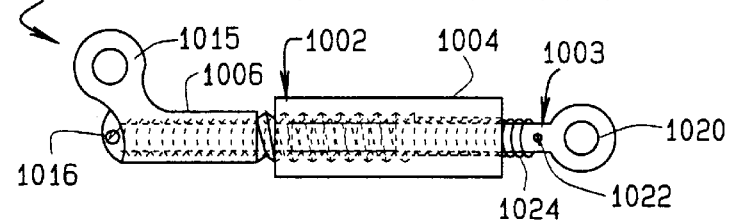
FIG. 34B is a side elevational view of the contraction sheath connector of FIG. 34A

Referring to FIGS. 34A and 34B, connector 1000 includes an outer, telescoping sheath 1002 and a contraction rod 1003 slidably engaged in the sheath. The sheath 1002 has a first or anterior tube section 1004 and second or posterior concentric tube section 1006. Anterior tube section 1004 has an inner bore 1008 extending the axial length of the section. In a preferred embodiment, a posterior portion of bore 1008 is has a threaded surface 1010. The entire bore could be threaded. The anterior tube section 1004 includes an opening 1011 or other structure for the engagement of a tool to facilitated rotation of the anterior section and elongation of the connector, as will be discussed below.

The posterior tube section 1006 of the sheath includes an inner bore 1012 that extends the axial length of the section. In a preferred embodiment, an anterior portion of the outer surface of section 1006 is a threaded surface 1014. The entire length of the surface could be threaded. There is a pivot eyelet 1015 on the posterior end of the posterior sheath section 1006. Eyelet 1015 is designed to attach to a maxillary apparatus, such as one described above. It will be noted that eyelet 1015 extends upwardly from, and at an angle to the posterior tube section. This design facilitates attachment of the eyelet to a maxillary appliance, as will be explained.

The eyelet 1015 can be attached to the maxillary apparatus by a pivot mounting boss which is described in greater detail in U.S. Pat. No. 6,036,488, which is incorporated herein by reference. There also can be a smaller eyelet 1016, or other spring attachment means, on the posterior end of section 1006 adjacent the posterior opening into the bore. Tube section 1006 is sized to fit in bore 1008 with its outer threaded surface 1014 engaging the inner threaded surface 1010 of the bore 1008 of the forward tube section 1004. When sections 1004 and 1006 are threadedly engaged, bores 1008 and 1012 form a bore through the axial length of the sheath of a substantially uniform diameter.

Rod 1003 has an elongated cylindrical body section 1018 with an eyelet 1020 at its anterior end for attachment to a mandibular device directly or, preferably, by a pivotal mounting boss of the type previously described. Rod 1003 can be solid or tubular and the body section is sized so as to be slidably engaged in the bore of the sheath with a spring around it, as described below. There can be a spring attachment structure 1022, such as small hole or other structure, on the anterior end of the rod adjacent eyelet 1020 to which the anterior end of a spring 1024 is attached. It will be noted that, alternatively, the spring can be welded directly to the rod by laser welding for example, preferably the spring is a nickel-titanium, closed coil spring. Spring 1024 is position around body section 1018.

In use, the connector is expanded to extend between a maxillary apparatus and mandibular apparatus, for example the anterior tube section 1004 is advanced to a distance that corresponds to the mandibular first bicuspid or a lower arch attachment sight on a mandibular apparatus. The connector is attached to the maxillary apparatus at eyelet 1014. Rod 1003, with spring 1024 around it, is inserted into the anterior end of the sheath and connected to the mandibular apparatus at eyelet 1020. The posterior end of the spring 1024 is attached to the posterior end of the sheath at eyelet 1016 or by other means such as welding. The sheath is connected to the maxillary apparatus at eyelet 1015. The spring 1024 exerts a contracting force on the rod and, consequently, on the mandibular apparatus. The spring is further activated, or the tension increased, by advancing the anterior tube section 1004 of the sheath by rotating it about the threads 1014 on the posterior in the appropriate direction so as to cause the sheath to telescope or increase in length and thereby stretch spring 1024. This rotation can be facilitated by inserting a tool in opening 1011 or other appropriate means. It will be appreciated that the sheath can be shortened to lessen the spring tension by rotating anterior tube section 1004 in the opposite direction. In any event, the connector can be adjusted to provide the desired tension on the mandibular apparatus required to correct the underbite at any stage of correction.

Figure 35A:
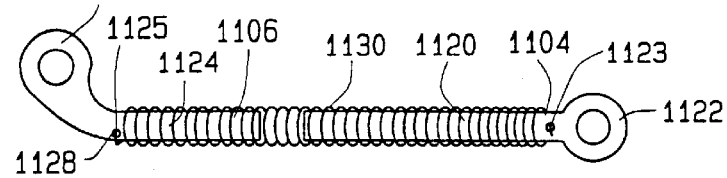
FIG. 35A is a side elevational view of a two-part rod for another embodiment of a novel contraction sheath connector of the present invention.
Figure 35B:
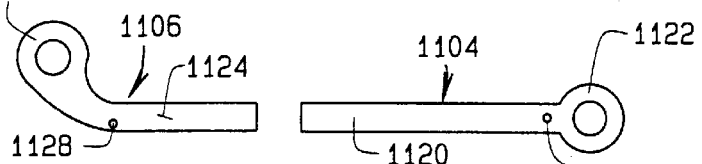
FIG. 35B illustrates the two inner rod sections of the two part, without a spring.
Figure 35C:
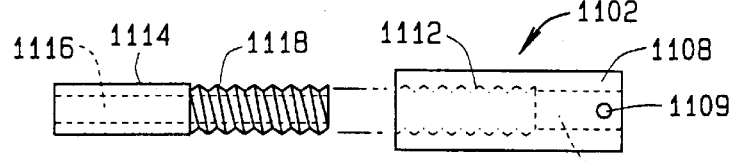
FIG. 35C is an exploded side elevational view of the sheath component that houses the two part rod in the contraction sheath connector of the present invention.
Figure 36:
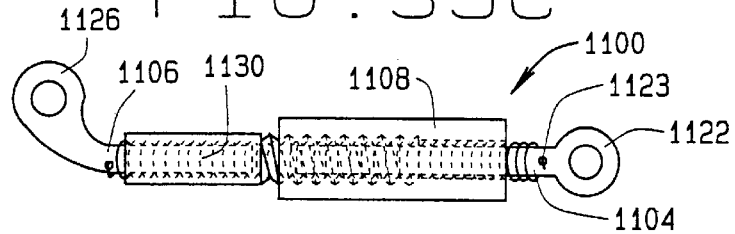
FIG. 36 is a side elevational view of the assembled contraction sheath connector of FIGS. 35A and 35B.

FIGS. 35A through 36 illustrate another embodiment of the contraction sheath connector of the present invention, indicated generally be reference numeral 1100. The connector 1100 has a telescoping outer sheath component 1102 with a first or anterior inner rod section 1104 and an opposed, second or posterior inner rod section 1106 slidably engaged therein. Sheath 1102 has an anterior tube section 1108 with an inner bore 1110 extending the axial length thereof. A posterior segment of the bore 1110 has a threaded surface 1112. The entire surface of the bore could be threaded. Anterior tube section 1108 can include an opening 1109 or other structure for the engagement of a tool to facilitate rotation of the anterior tube section. Sheath 1102 also includes a posterior tube section 1114 concentric to the anterior tube section. Posterior tube section 1114 has an inner bore 1116 running the axial length of the tube. Tube section 1114 has a threaded outer surface 1118 on its anterior end. The entire outer surface of the posterior tube section can be threaded. Posterior tube section 1114 is sized so as to be threadedly engaged within bore 1110 of the anterior tube section. It will be appreciated that when the tube sections are engaged bores 1110 and 1116 cooperate to form a bore through the axial length of sheath 1102 of a substantially uniform diameter.

Rod section 1104 has an elongated cylindrical body 1120 which can be solid or tubular. Body 1120 has an appliance attachment eyelet 1122 at its anterior end. A spring attachment structure 1123 is positioned adjacent eyelet 1122. Structure 1123 can be an opening for the engagement of one end of a coil spring, or any other structure that will secure one end of a spring. The spring could be welded in place. Rod section 1106 also has an elongated cylindrical body 1124 of the substantially same diameter as body 1120. There is an attachment eyelet 1126 on the posterior end of rod section 1106. Eyelet 1126 extends generally upwardly from, and at an angle to, body 1124 to facilitate attachment of the eyelet to a maxillary appliance. There is a spring attachment structure or opening 1128 adjacent eyelet 1126. The respective rod bodies 1120 and 1124 are sized to be slidingly engaged within the sheath bore with a spring around them. A coil spring 1130 is coiled around cylindrical bodies 1120 and 1124, respectively, and attached at its anterior end to structure 1123 and at its posterior end at structure 1128. The diameter of the spring is sized to encircle the rod bodies within the outer sheath bore without impingement. The spring, preferably a nickel-titanium spring, exerts a contracting force on the rod sections drawing them towards one another within the sheath bore.

In use, connector 1100 is expanded to extend between a maxillary apparatus and mandibular apparatus, for example the anterior section 1108 is advanced by rotation around the threaded end of the posterior tube section to a distance that corresponds to the mandibular first bicuspid or a lower arch attachment sight on a mandibular apparatus. Eyelet 1126 is attached to a pivot on the maxillary appliance and eyelet 1122 is attached to a pivot on the mandibular appliance. The contracting force of the spring causes the posterior rod section 1106 to exert a forward force on the maxillary appliance and causes the anterior rod section 1104 to exert a distalizing force on the mandibular apparatus. The amount of force can be adjusted by adjusting spring tension, either by replacing the spring or by lengthening or shortening the telescoping sheath.

Figure 37:
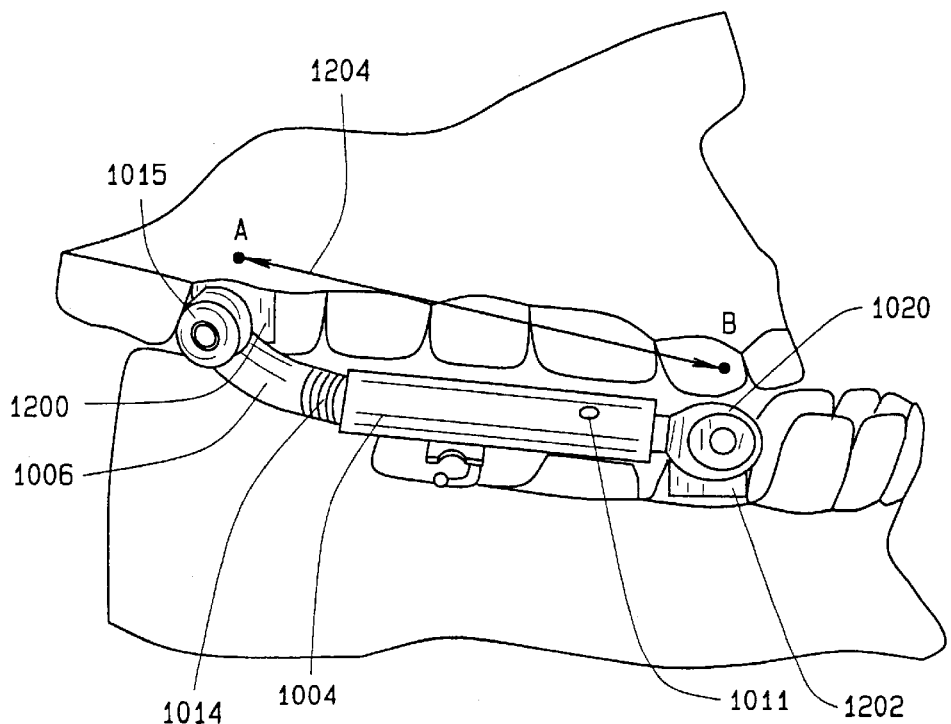
FIG. 37 illustrates a contraction sheath connector of the present invention in use in a first starting position
Figure 38:
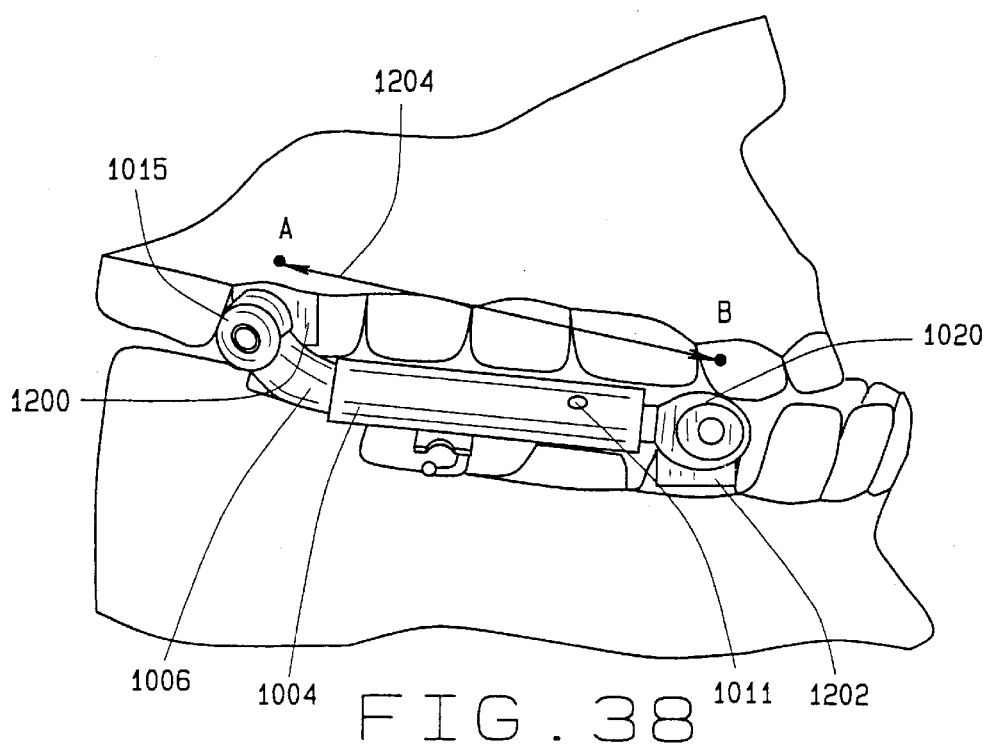
FIG. 38 illustrates a contraction sheath connector of the present invention in use in a second or finished position.

FIG. 37 illustrates a contracting sheath connector 1000 of the present invention attached between a maxillary apparatus 1200, corresponding to position A and a mandibular apparatus 1202 corresponding to point B. The connector preferably is connected to the respective apparatus at a pivot. The connector is in a starting position for the correction of a severe underbite. It will be appreciated that connector 1000 or connector 1100 may be employed as shown. The spring biased rod 1003 of the connector exerts a contracting force on the mandible, as described above, shortening the distance between point A and point B as represented by arrow 1204. As the underbite corrects, anterior tube section 1004 is rotated about the threads to shorten the sheath. FIG. 38 shows a finished position of contraction connector 1000 when the underbite is corrected. It can be seen that the telescoping sheath 1002 has been shortened to accommodate the decrease in distance between points A and B as represented by arrow 1204. It will be recognized that when connector 1100 is employed as shown in FIGS. 37 and 38, the spring biased rod sections 1104 and 1106 will exert a contracting force on both the maxilla and the mandible, drawing points A and B toward each other so as to correct the underbite.

Figure 39A:
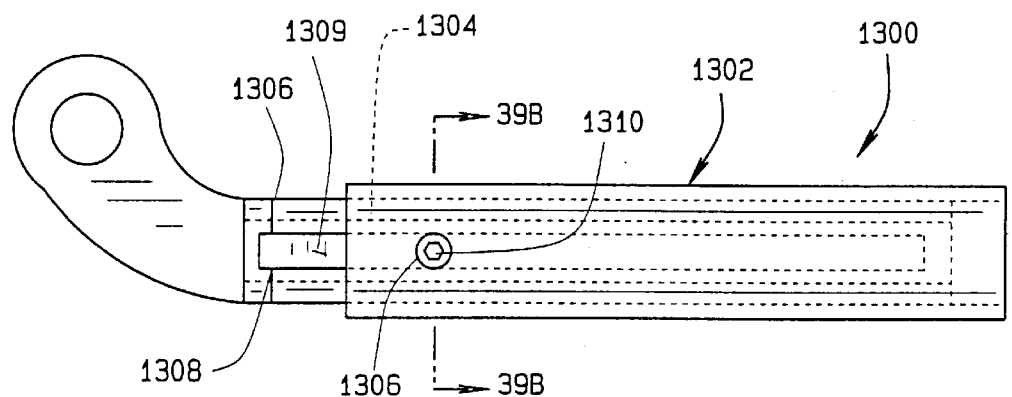
FIG. 39A is a side elevational view of an advancing sheath of the present invention including a novel channel lock feature of the present invention.
Figure 39B:
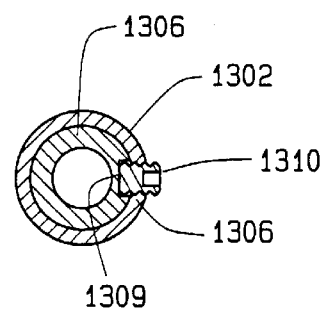
FIG. 39B is a cross-sectional view taken along line 39B—39B of FIG. 39A.

A novel channel lock connector of the present invention is indicated by reference numeral 1300 in FIGS. 39A and 39B. The channel lock connector indicated generally by number 1300, primarily is employed with advancing sheaths, such as those disclosed in U.S. Pat. No. 5,919,042, which is incorporated herein by reference. It will be understood, however, that a channel lock connector 1300 can be used in any of the sheaths described above without departing from the scope of the invention.

Channel lock connector 1300 has an outer sheath 1302 with an axial bore 1304. The surface of bore 1304 is threaded. An externally threaded inner tube 1306 is threadedly engaged in bore 1304. As explained above, the outer tube 1302 can be rotated about the threads to advance or retract the outer sheath to change the length of the connector. In the illustrated embodiment, the outer sheath 1302 has a threaded set screw hole 1306 formed through the wall, adjacent its posterior end. Inner tube 1306 has an external channel 1308 having a floor 1309 running the approximate axial length of the inner tube. Hole 1306 is aligned with channel 1308. A threaded set screw 1310 or the like, is threadedly engaged in hole 1306. The outer sheath the set screw can be tightened, with an Allen wrench for example, to engage the channel so as to impinge the channel floor 1309 and secure the outer sheath in position and to prevent the advancing or back threading of the sheath.

Alternative embodiments of the channel lock connector 1300 are included within the scope of the invention. For example, a series of evenly spaced apart openings or holes, threaded or unthreaded, can be formed in the floor 1309 of channel 1308. Locking pins, threaded or unthreaded, can be inserted through hole 1306 (which also may be formed in an unthreaded embodiment) to secure the outer sheath in the desired position.

In view of the above, it will be seen that the several objects and advantages of the present invention have been achieved and other advantageous results have been obtained. Furthermore, since various changes and modifications may be made in the assemblies of the present invention without departing from the scope of the claims, the foregoing description and accompanying drawings are intended to be illustrative only and should not be construed in a limiting sense.

What is claimed is:

1. A contracting connector for connection between a maxillary appliance and a mandibular appliance for the treatment of an underbite in a subject in need of such treatment, comprising:
    a tubular body having an inner bore therein, said tubular body having an maxillary appliance attachment at a posterior end thereof; the tubular body being a telescoping tubular body comprising an externally threaded posterior tube section and an internally threaded anterior tube section threadedly engaged on said posterior tube section;
    a rod slidingly engaged in the bore of the body, said rod having a mandibular appliance attachment at an anterior end thereof;
    a spring connected to the rod and extending through the bore, said spring connected to the posterior end of the tubular body whereby the spring causes contraction pressure on the rod and the mandibular appliance;
    whereby rotation of the tubular body outer tube section in a first direction lengthens the tubular body to increase the contraction pressure of the spring and rotation of the tubular body outer tube in an opposite direction shortens the tubular to decrease contraction pressure of the spring.

2. The connector of claim 1 wherein said maxillary appliance attachment is an eyelet.

3. The connector of claim 2 wherein said anterior tube section has an opening formed therein for the engagement of a device to facilitate rotation of the anterior tube section.

4. The connector of claim 1 wherein said mandibular appliance attachment is an eyelet.

5. The connector of claim 1 wherein said spring is a nickel-titanium spring.

6. A contracting connector for connection between the maxilla and the mandible for the treatment of an underbite in a subject in need of such treatment, comprising;
    a tubular body having a inner lumen, said tubular body being a telescoping tubular body;
    an anterior rod and a posterior rod slidingly engaged in the lumen, said posterior rod being attachable to the maxilla and said anterior rod being attachable to the mandible; and
    a spring connected between the anterior rod and posterior rod within the lumen whereby the spring exerts contracting pressure on the two rod sections.

7. The connector of claim 6 wherein the tubular body further comprises an externally threaded posterior tube section and an internally threaded anterior tube section threadedly engaged on said posterior tube section whereby rotation of the outer tube section in a first direction lengthens the tubular body to increase contracting pressure of the spring and rotation of the outer tube in an opposite direction shortens the tubular body to decrease contracting pressure of the spring.

8. The connector of claim 7 wherein said anterior tube section has a opening formed therein for the engagement of a device to facilitate rotation of the anterior tube section.

9. The connector of claim 6 wherein said posterior rod has an eyelet at a posterior end.

10. The connector of claim 6 wherein said anterior rod has an eyelet at an anterior.

11. The connector of claim 6 wherein said spring is a nickel-titanium spring.

12. A contracting sheath device for connecting the mandible to the maxilla to correct an underbite in a subject in need of such correction, comprising:
    an adjustable hollow sheath, said sheath having an externally threaded posterior section and an internally threaded anterior section, said anterior section threadedly engaging said posterior section whereby rotation of said anterior section in one direction lengthens the sheath and rotation in an opposite direction shortens the sheath, said sheath including an eyelet at a posterior end thereof, the eyelet being attachable to a maxillary apparatus;
    a rod slidingly engaged within the sheath, said rod having an eyelet at an anterior end thereof, the eyelet being attachable to a mandibular apparatus; and
    a spring coiled around said rod and extending between the posterior end of said sheath and the anterior end of said rod, said spring disposed to urge said rod rearwardly relative to said sheath, thereby exerting an underbite corrective pressure on the mandible.

13. The connector sheath of claim 12 wherein the spring is a nickel titanium spring.

14. The connector sheath of claim 12 further comprising means on said anterior section of said hollow sheath to facilitate the rotation of said anterior section.

15. A contracting sheath device for connecting the mandible to the maxilla to correct an underbite in a subject in need of such correction, comprising:
    an adjustable hollow sheath, said sheath having an externally threaded posterior section and an internally threaded anterior section, said anterior section threadedly engaging said posterior section whereby rotation of said anterior section in one direction lengthens the sheath and rotation in an opposite direction shortens the sheath; apparatus;
    an anterior rod slidingly engaged within the sheath and an opposed posterior rod slidingly engaged within the sheath, said anterior rod having an eyelet at an anterior end thereof attachable to a mandibular apparatus, said posterior rod having an eyelet at a posterior end thereof attachable to a maxillary apparatus; and
    a spring connected between said anterior and posterior rods, said spring disposed to exert a contracting pressure on said anterior rod and said posterior rod, thereby exerting an underbite corrective pressure on the maxilla and the mandible.

16. The connector sheath of claim 15 wherein the spring is a nickkel-titanium spring.

17. The connector sheath of claim 15 further comprising means on said anterior section of said hollow sheath to facilitated the rotation of said anterior section.

18. An orthodontic device for connecting the mandible to the maxilla to correct an underbite in a subject in need of such correction, comprising:
    a maxillary apparatus for attachment to the maxilla of the subject;
    a mandibular apparatus for attachment to the mandible of the subject;
    at least one contracting connector attached between said maxillary apparatus and said mandibular apparatus, said contracting connector including an adjustable hollow sheath, said sheath having an externally threaded posterior section and an internally threaded anterior section, said anterior section threadedly engaging said posterior section whereby rotation of said anterior portion in one direction lengthens the sheath and rotation in an opposite direction shortens the sheath, said sheath including an eyelet at a posterior end thereof, the eyelet being attachable to the maxillary apparatus; a rod slidingly engaged within the sheath, said rod having an eyelet at an anterior end thereof, the eyelet being attachable to the mandibular apparatus; and a spring coiled around said rod and extending between the posterior end of said sheath and the anterior end of said rod, said spring disposed to urge said rod posteriorly relative to said sheath, thereby exerting an underbite corrective pressure on the mandible.

19. The device of claim 18 further comprising a second contracting connector on a side of the device opposite the at least one contracting connector.

20. The device of claim 18 wherein the spring is a nickel titanium spring.

21. The device of claim 18 wherein said hollow sheath has at least one threaded opening formed therein and said rod has a channel formed therein extending along the outer axial length of the rod and positioned adjacent the at least one threaded opening, and a locking screw threadedly engaged in said at least one threaded opening whereby said locking screw is disposed to engage said channel when rotated in first direction so as to impinge said rod and secure said rod in a selected position within said hollow sheath.

22. An orthodontic device for connecting the mandible to the maxilla to correct an underbite in a subject in need of such correction, comprising:

a maxillary apparatus for attachment to the maxilla of the subject;

a mandibular apparatus for attachment to the mandible of the subject;

at least one contracting connector attached between said maxillary apparatus and said mandibular apparatus, said contracting connector including an adjustable hollow sheath, said sheath having an externally threaded posterior section and an internally threaded anterior section, said anterior section threadedly engaging said posterior section whereby rotation of said anterior section in one direction lengthens the sheath and rotation in an opposite direction shortens the sheath; an anterior rod slidingly engaged within the sheath and an opposed posterior rod slidingly engaged within the sheath, said anterior rod having an eyelet at an anterior end thereof attachable to the mandibular apparatus, said posterior rod having an eyelet at a posterior end thereof attachable to the maxillary apparatus; and a spring connected between said anterior and posterior rods, said spring disposed to exert a contracting pressure and said anterior rod and said posterior rod, thereby exerting an underbite corrective pressure on the maxilla and the mandible.

23. The device of claim 22 further comprising a second contracting connector on a side of the device opposite the at least one contracting connector.

24. The device of claim 22 wherein the spring is a nickel-titanium spring.

25. In an orthodontic device having a maxillary apparatus, a mandibular apparatus and at least one adjustable connector between the maxillary apparatus and the mandibular apparatus, the adjustable connector including an outer hollow sheath and a spring-biased tube within the sheath, the improvement comprising:

said outer hollow sheath having at least one opening formed therein and said inner tube having a channel formed therein extending along the outer axial length of the tube and positioned adjacent the at least one opening in the outer hollow sheath; and a locking structure engaged in said at least one opening in the outer hollow sheath, said locking structure disposed to engage said channel and secure said sheath in a desired position relative to said inner tube; said channel including a plurality of linerally aligned locking structure engagement openings formed therein.

26. The improvement of claim 25 wherein said locking structure is a locking pin.

27. The improvement of claim 24 wherein each of said plurality of linerally aligned locking structure engagement openings has internal threads therein and said locking pin has external threads thereon.

\* \* \* \* \*